United States Patent
Boris et al.

(10) Patent No.: US 8,246,660 B2
(45) Date of Patent: Aug. 21, 2012

(54) BONE PLATE AND METHOD FOR USING BONE PLATE

(75) Inventors: Olevsky Boris, Fairlawn, NJ (US);
Kevin C. Booth, Alamo, CA (US);
Joseph M. Grant, Danville, CA (US)

(73) Assignee: Blackstone Medical, Inc., Lewisville, TX (US)

( * ) Notice: Subject to any disclaimer, the term of this patent is extended or adjusted under 35 U.S.C. 154(b) by 789 days.

(21) Appl. No.: 11/092,273

(22) Filed: Mar. 29, 2005

(65) Prior Publication Data
US 2005/0251138 A1    Nov. 10, 2005

Related U.S. Application Data

(63) Continuation-in-part of application No. 10/968,585, filed on Oct. 19, 2004, now abandoned.

(60) Provisional application No. 60/512,653, filed on Oct. 20, 2003.

(51) Int. Cl.
*A61B 17/80* (2006.01)
(52) U.S. Cl. ........................ 606/280; 606/246
(58) Field of Classification Search .............. 606/69–71, 606/280–299; 623/17.11
See application file for complete search history.

(56) References Cited

U.S. PATENT DOCUMENTS

| | | | |
|---|---|---|---|
| 4,422,451 A | 12/1983 | Kalamchi | |
| 4,488,543 A * | 12/1984 | Tornier | 606/65 |
| 5,423,826 A * | 6/1995 | Coates et al. | 606/96 |
| 5,487,741 A * | 1/1996 | Maruyama et al. | 606/60 |
| 5,630,816 A * | 5/1997 | Kambin | 606/252 |
| 5,851,207 A * | 12/1998 | Cesarone | 606/69 |
| 6,080,157 A | 6/2000 | Cathro et al. | |
| 6,398,785 B2 * | 6/2002 | Carchidi et al. | 606/916 |
| 6,428,542 B1 * | 8/2002 | Michelson | 606/70 |
| 6,436,103 B1 * | 8/2002 | Suddaby | 606/96 |
| 6,635,087 B2 | 10/2003 | Angelucci et al. | |
| 6,660,007 B2 | 12/2003 | Khanna | |
| 6,712,852 B1 | 3/2004 | Chung et al. | |
| 6,945,974 B2 * | 9/2005 | Dalton | 606/70 |
| 7,077,844 B2 * | 7/2006 | Michelson | 606/71 |
| 2002/0120335 A1 | 8/2002 | Angelucci et al. | |
| 2003/0045935 A1 | 3/2003 | Angelucci et al. | |
| 2003/0083747 A1 * | 5/2003 | Winterbottom et al. | 623/17.11 |
| 2003/0125738 A1 | 7/2003 | Khanna | |
| 2003/0125740 A1 | 7/2003 | Khanna | |
| 2004/0030388 A1 | 2/2004 | Null et al. | |
| 2004/0153155 A1 | 8/2004 | Chung et al. | |
| 2004/0186482 A1 * | 9/2004 | Kolb et al. | 606/96 |
| 2004/0210222 A1 * | 10/2004 | Angelucci et al. | 606/69 |

FOREIGN PATENT DOCUMENTS

WO    WO 2004/017837    3/2004

OTHER PUBLICATIONS

Supplementary Partial European Search Report, European Application No. 05 73 0243, dated Dec. 3, 2009.

\* cited by examiner

*Primary Examiner* — Eduardo C Robert
*Assistant Examiner* — Mary Hoffman
(74) *Attorney, Agent, or Firm* — Baker & McKenzie LLP

(57) ABSTRACT

Disclosed is an apparatus placed by an implantation tool for spacing a first section of a divided lamina apart from a second section of the divided lamina in connection with a laminoplasty procedure, including an apparatus placed with an implantation tool and fastened in place by a locking plate that is held in place by a locking plate fastener driven into the tool receiving hole in the apparatus.

34 Claims, 11 Drawing Sheets

BONE PLATE AND METHOD FOR USING BONE PLATE

CROSS-REFERENCE TO RELATED APPLICATIONS

This application is a continuation in part of U.S. application Ser. No. 10/968,585, filed Oct. 19, 2004 now abandoned, which claims the benefit under 35 U.S.C. 119(e) of U.S. Provisional Application Ser. No. 60/512,653, filed Oct. 20, 2003

FIELD OF THE INVENTION

Various embodiments of the present invention relate to a bone plate apparatus and methods for using the bone plate apparatus.

More particularly, in one embodiment the bone plate apparatus and/or method may be used in connection with a laminoplasty procedure.

BACKGROUND OF THE INVENTION

Examples of various patent documents in the laminoplasty area include the following:

U.S. patent Publication No. 20040030388 in the name of Null et al. relates to laminoplasty devices and methods. More particularly, laminoplasty plates are engageable to at least one portion of a divided lamina to maintain a desired spacing relative to the spinal canal. The laminoplasty plates include a spacer portion having a first end and a second end that spans a gap formed by at least one of a divided lamina portion. The laminoplasty plates can include a lamina engagement portion at one end for engagement with the divided lamina portion.

U.S. Pat. No. 6,080,157 to Cathro et al. relates to a device to stabilize the lamina. More particularly, a device for dynamically stabilizing the lamina after a laminoplasty includes a spacer which is shaped to engage between the severed edges of the lamina. The device also includes a retainer attached to the spacer which is adapted to maintain the spacer in an operative position. A method of dynamically stabilizing the lamina after a laminoplasty is also provided, which includes the steps of positioning the spacer between the severed edges of the lamina, and positioning the retainer to maintain the spacer in the operative position.

U.S. patent Publication No. 20030125738 in the name of Khanna relates to a laminoplasty with laminar stabilization method and system. More particularly, fixation devices and methods for stabilization of the lamina after laminoplasty are described. The device comprises a plate with several holes that receive bone fasteners. The plate is curved at the ends to contour to the vertebral structure and has appendages to engage the displaced lamina in a fixed position. Alternatively, the plate has a bone fusion spacer in the middle to engage and fuse the lamina in the displaced position. Several methods of dynamically stabilizing the lamina after either the open door, double door or expansive laminoplasty technique are provided.

U.S. Pat. No. 6,712,852 to Chung et al. relates to a laminoplasty cage. More particularly, a medical implant device for use in spinal surgery, and more preferably for use in laminoplasty surgery is provided. The implant is a cage-like member having a generally hollow, elongate body with open ends. The implant is formed from a generally hollow, elongate body having four sides: opposed cephalad and caudal sides, and opposed posterior and anterior sides adjacent to the cephalad and caudal sides. The four sides extend along a longitudinal axis, and define an inner lumen extending between opposed first and second open ends.

U.S. Pat. No. 6,635,087 to Angelucci et al. relates to laminoplasty implants and methods of use. More particularly, implants for use in the spinal column are disclosed. The implants comprise a bone allograft coupled with a non-allogenic plate. The plate has ends that fasten to opposing spine segments, and an intermediate portion that engages the allograft using deformable fingers, or with a hollow portion sized to receive and hold part of the allograft, or with fixed tabs. Methods of using the implants are also disclosed.

U.S. patent Publication No. 20030045935 in the name of Angelucci et al. relates to laminoplasty implants and methods of use. More particularly, implants for maintaining a distance between cut spinal bones are disclosed. The implants are made of metal, polymer or bone allograft, and have ends angled with respect to each other to conform to the cut bone ends. The implants have hollow regions for packing osteogenic material. The implant ends have surface projections to reduce slippage. Implants made of bone allograft also have ends made of demineralized bone to speed fusion between spine and implant. Methods of using the implants are also disclosed.

U.S. patent Publication No. 20020120335 in the name of Angelucci et al. relates to laminoplasty implants and methods of use. More particularly, implants for maintaining a distance between cut spinal bones are disclosed. The implants are made of metal, polymer or bone allograft having ends configured to conform to the cut bone ends. The implants have hollow regions for packing osteogenic material. The implant ends have surface projections to reduce slippage. Implants made of bone allograft also have spine contacting ends made of demineralized bone to speed fusion of spine and implant; they may also have bone flaps to fix the implant to the spine. Methods of using the implants are also disclosed.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
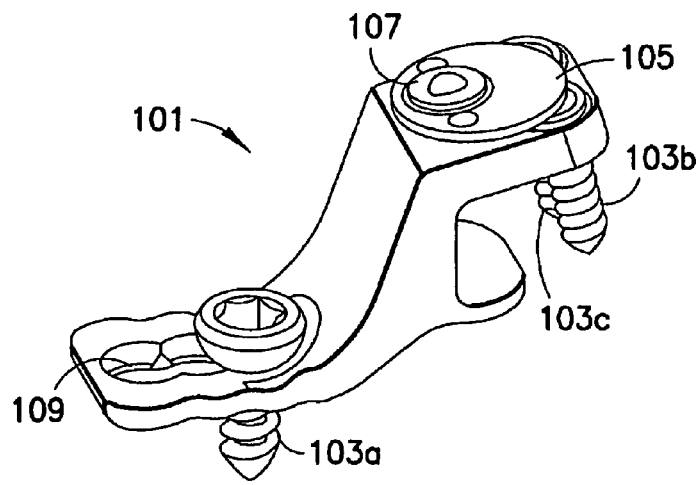
FIG. 1 shows a perspective view of one embodiment of a bone plate apparatus according to the present invention.
Figure 2A:
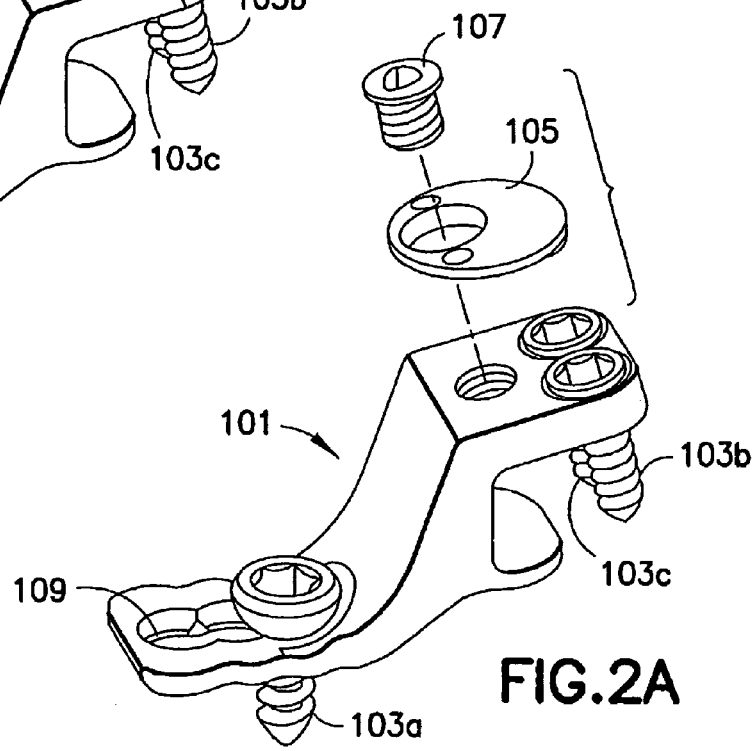
FIGS. 2A and 2B show exploded perspective views of the bone plate apparatus of FIG. 1 (FIG. 2A shows the bone plate apparatus from one angle and FIG. 2B shows the bone plate apparatus from another angle)
Figure 2B:
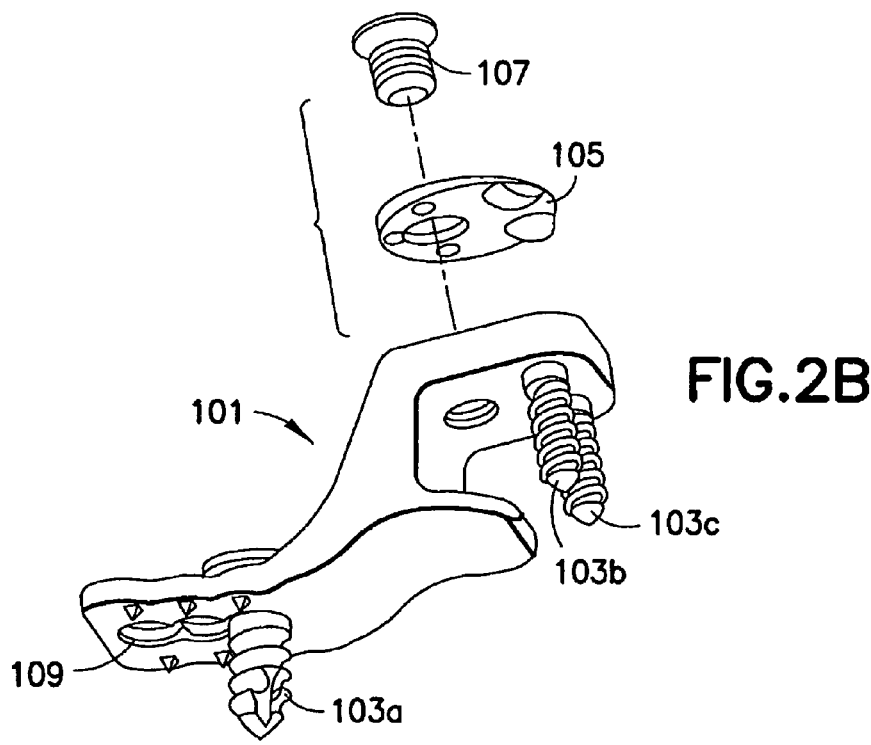

Referring now to FIG. 1 (as well as FIGS. 2A and 2B, showing exploded perspective views of the bone plate apparatus of FIG. 1), one embodiment of a bone plate apparatus according to the present invention is shown. As seen in these Figs., Bone Plate 101 may be attached to bone using Bone Screws 103a, 103b and 103c. In one example (which example is intended to be illustrative and not restrictive), Bone Plate 101 may have a length between 20 mm and 30 mm (e.g., Bone Plate 101 may be provided in a number of distinct lengths). In another example (which example is intended to be illustrative and not restrictive), each of Bone Screws 103a, 103b and 103c may be a self-tapping bone screw. In another example (which example is intended to be illustrative and not restrictive), each of Bone Screws 103a, 103b and 103c may have a diameter selected from the group including (but not limited to) 1.5 mm, 2.0 mm and 2.7 mm. In another example (which example is intended to be illustrative and not restrictive), each of Bone Screws 103a, 103b and 103c may have a length from 4 mm to 8 mm, in 0.1 mm increments.

Further, Locking Plate 105 (which may itself be held in place by Fastener 107 (e.g., a machine screw)) may be used to help prevent screw back-out (FIGS. 2A and 2B show use of Locking Plate 105 and Fastener 107 most clearly).

Further still, Slot 109 (which may have distinct holding positions or detents (as shown in these Figs.), and/or which may not have such detents in order to allow essentially free positioning anywhere within the slot) may be provided to aid in adjustment to an individual patient's anatomy.

Further still, one or more protrusions (or "teeth") may be provided to aid in maintaining position during and/or after implantation (a number of such teeth are shown but not separately numbered in these Figs.).

Further still, the bottom profile may be streamlined as shown in these Figs. (e.g., in order to reduce the penetration inside the spine).

Figure 3A:
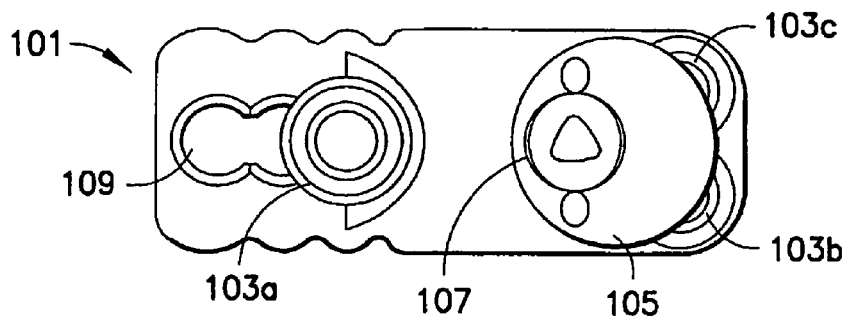
FIGS. 3A, 3B and 3C show, respectively, a plan view, a side elevational view and a front view of the bone plate apparatus of FIG. 1.
Figure 3B:
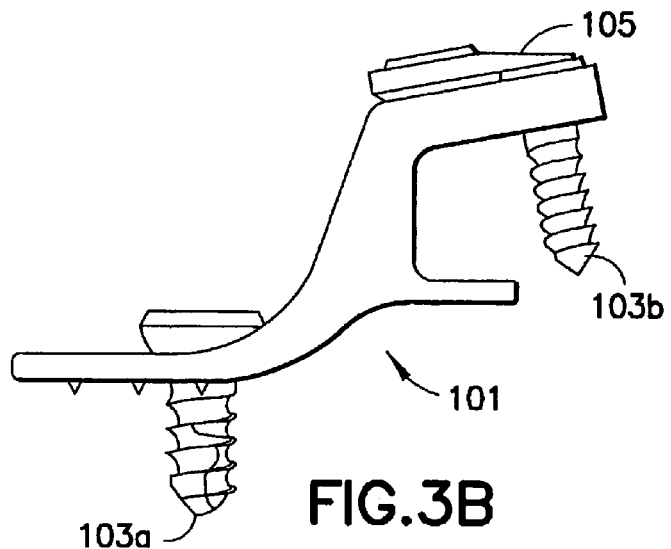
Figure 3C:
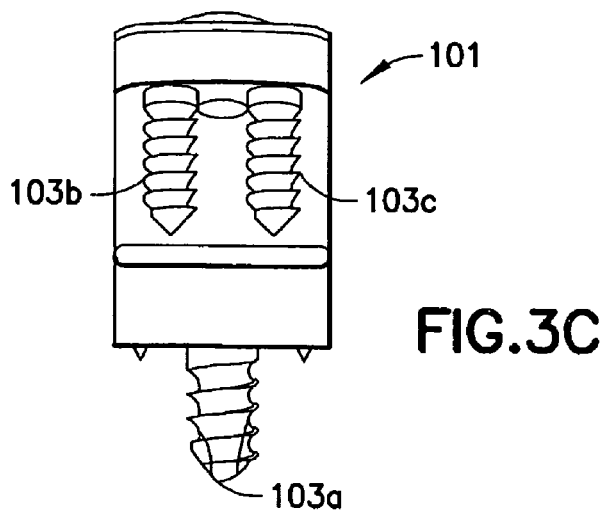

Referring now to FIGS. 3A, 3B and 3C, a plan view, a side elevational view and a front view of the bone plate apparatus of FIG. 1 are shown. Of note, the dimensions identified in these Figs. are, of course, illustrative and not restrictive.

Figure 4A:
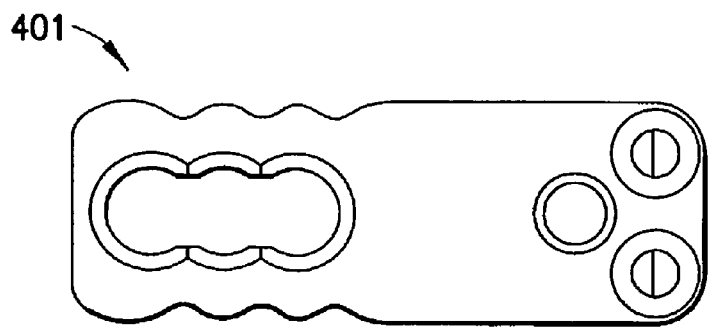
FIGS. 4A, 4B and 4C show, respectively, a plan view, a side elevational view and a front view of a bone plate apparatus according to another embodiment of the present invention.
Figure 4B:
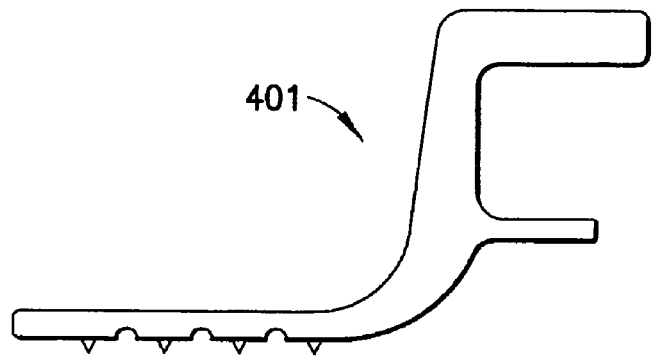
Figure 4C:
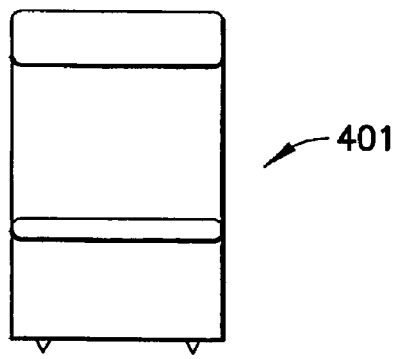

Referring now to FIGS. 4A, 4B and 4C, a plan view, a side elevational view and a front view of a bone plate apparatus according to an embodiment of the present invention are shown. Of note, these Figs. depict the bone plate apparatus without showing the bone screws. Of further note, the dimensions identified in these Figs. are, of course, illustrative and not restrictive.

Figure 5A:
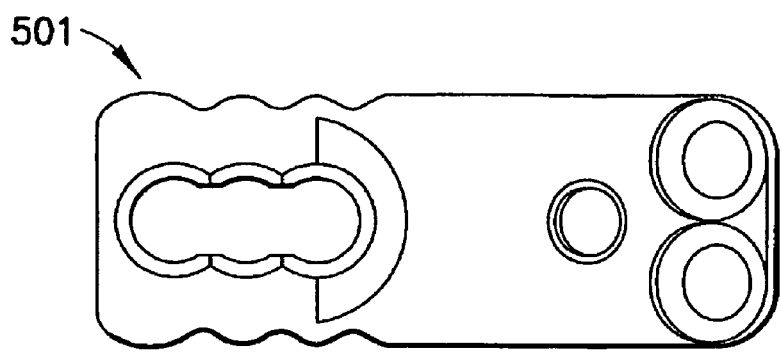
FIGS. 5A, 5B and 5C show, respectively, a plan view, a side elevational view and a front view of a bone plate apparatus according to another embodiment of the present invention.
Figure 5B:
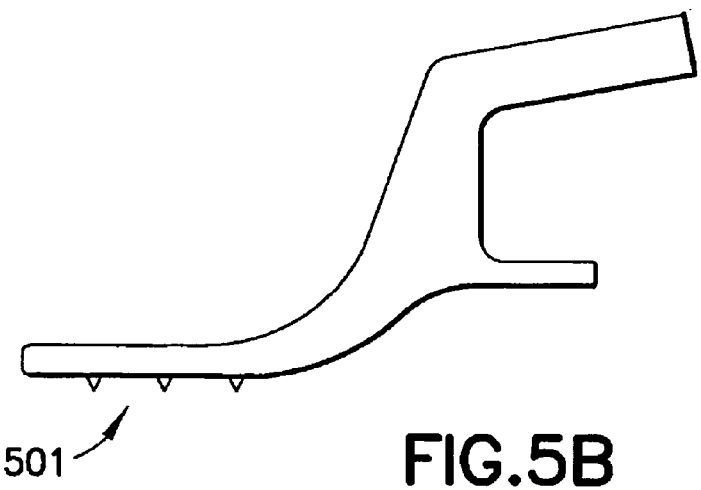
Figure 5C:
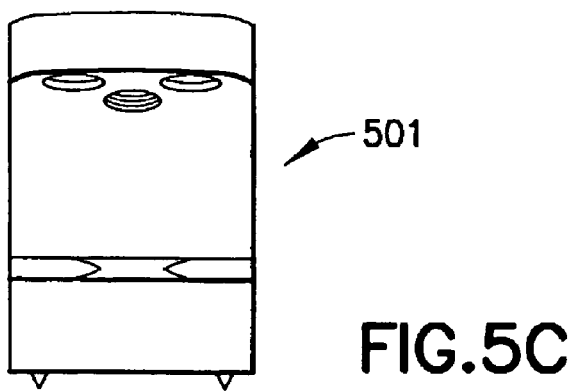

Referring now to FIGS. 5A, 5B and 5C, a plan view, a side elevational view and a front view of a bone plate apparatus according to an embodiment of the present invention are shown. Of note, these Figs. depict the bone plate apparatus without showing the bone screws. Of further note, the dimensions identified in these Figs. are, of course, illustrative and not restrictive.

Referring now to one example use of a bone plate apparatus according to the present invention (which example is intended to be illustrative and not restrictive), it is noted that under this example an "open door laminoplasty" (wherein the vertebrae are made to swing open like a door) may be simplified and/or stability may be maintained (such simplification/stability may be obtained by replacing and/or supplementing certain steps and/or components of a conventional laminoplasty with steps and/or components of the present invention (e.g., with an embodiment of the bone plate apparatus described herein). Such an open door laminoplasty is typically performed on a restricted spinal canal in the neck (e.g., a painfully restricted spinal canal), wherein the laminoplasty relieves pressure (e.g., immediately) by creating additional space for the spinal cord and roots.

More particularly, such a laminoplasty is typically performed as follows:

The surgeon makes an incision on the back of the patient's neck.

The surgeon creates a "hinge" by cutting a groove down one side of the cervical vertebrae.

The surgeon cuts all the way through the other side of the vertebrae.

In order to create room for the bones to open like a door, the surgeon removes the tips of the spinal process.

In order to take pressure off the spinal cord and roots, the surgeon bends open the back of each vertebrae (like a door on its hinge).

The surgeon places, in the opened space of the door, appropriately sized wedges made of bone.

The surgeon allows the door to swing shut. Since the wedges stop the door from closing all of the way, the spinal cord and roots receive additional space.

Figure 6:
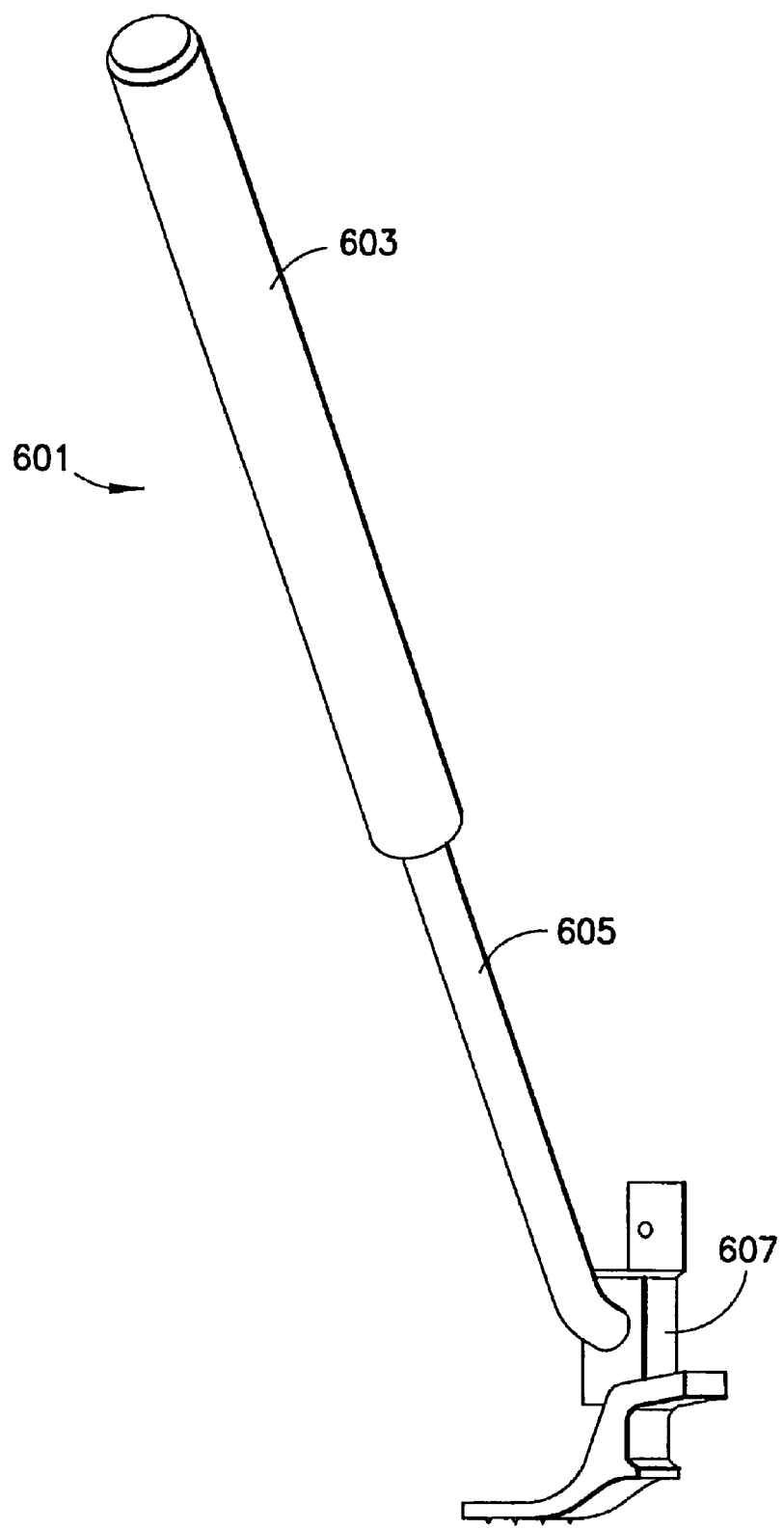
FIG. 6 shows a perspective view of a bone plate apparatus according to an embodiment of the present invention and an insertion tool associated therewith according to an embodiment of the present invention.

Referring now to FIG. 6, it is seen that Insertion Tool 601 may be used to aid insertion into a patient (e.g., to make placement quick and easy), and that Insertion Tool 601 may include Handle 603, Shaft 605 and Mounting Mechanism 607 (which may be used to hold a bone plate and/or to aid in turning the various screws associated with the bone plate).

Figure 7:
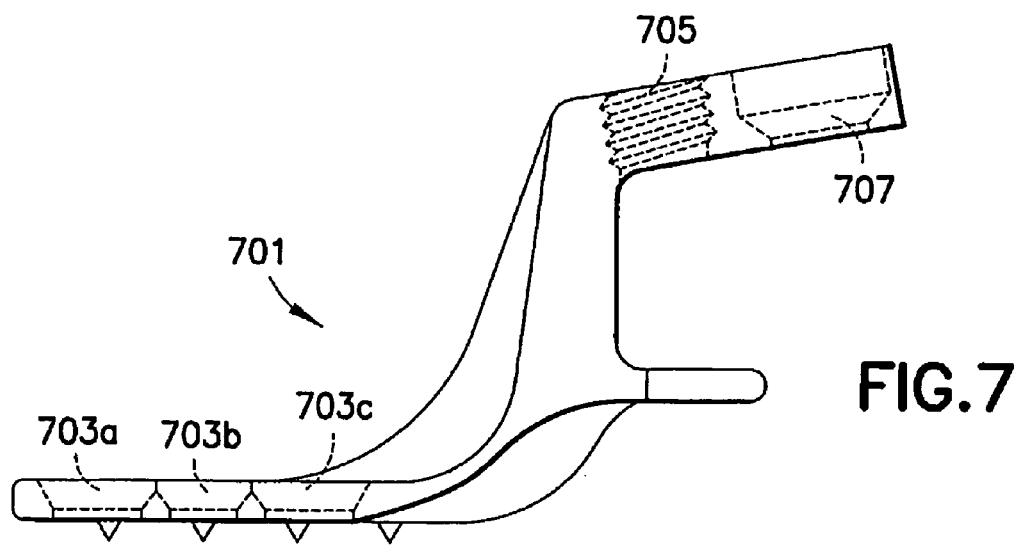
FIG. 7 shows a cut-away view of a bone plate apparatus according to an embodiment of the present invention.

Referring now to FIG. 7, a cut-away view of a bone plate apparatus according to an embodiment of the present invention is shown. Of note, this Fig. clearly shows Detents 703a, 703b and 703c as well as Machine Screw Retaining Thread 705.

Figure 8:
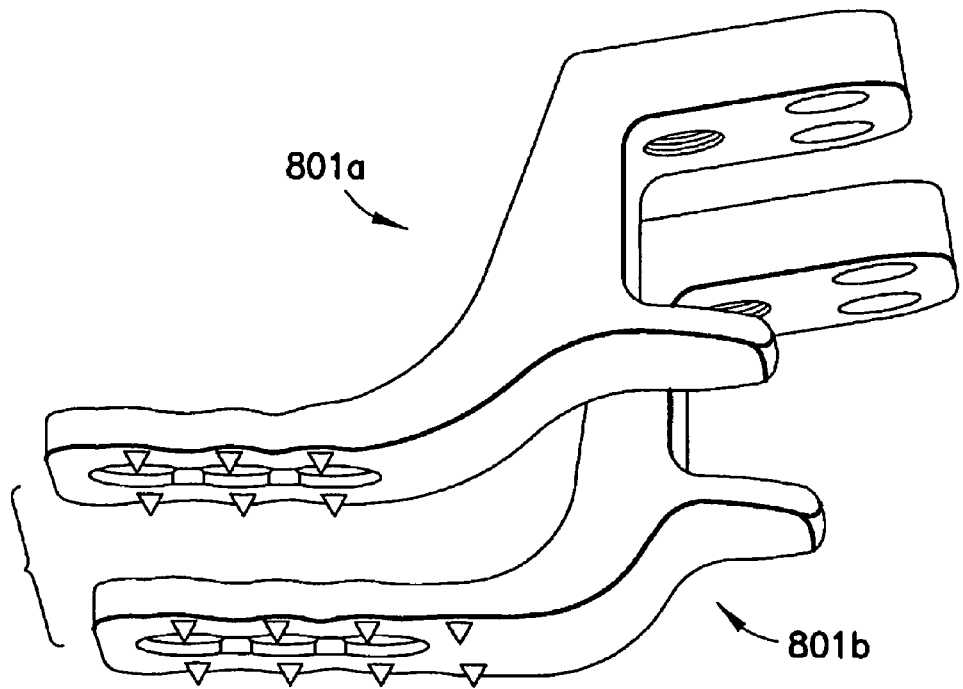
FIG. 8 shows another perspective view of two bone plate apparatus according to embodiments of the present invention.

Referring now to FIG. 8, another perspective view of two bone plate apparatus according to embodiments of the present invention are shown.

In another embodiment, some or all of the components may include or be made essentially entirely from a commercially pure material (e.g., Titanium and/or Alloy Titanium).

In another embodiment, Indications relating to use of the present invention may include (but not be limited to):

For use as laminoplasty plate for cervical spine (from C2-C7)

For use as orthognathic plate for fixation (e.g., permanent fixation) of bone segment(s) after a sagittal split Osteotomy.

Figure 9:
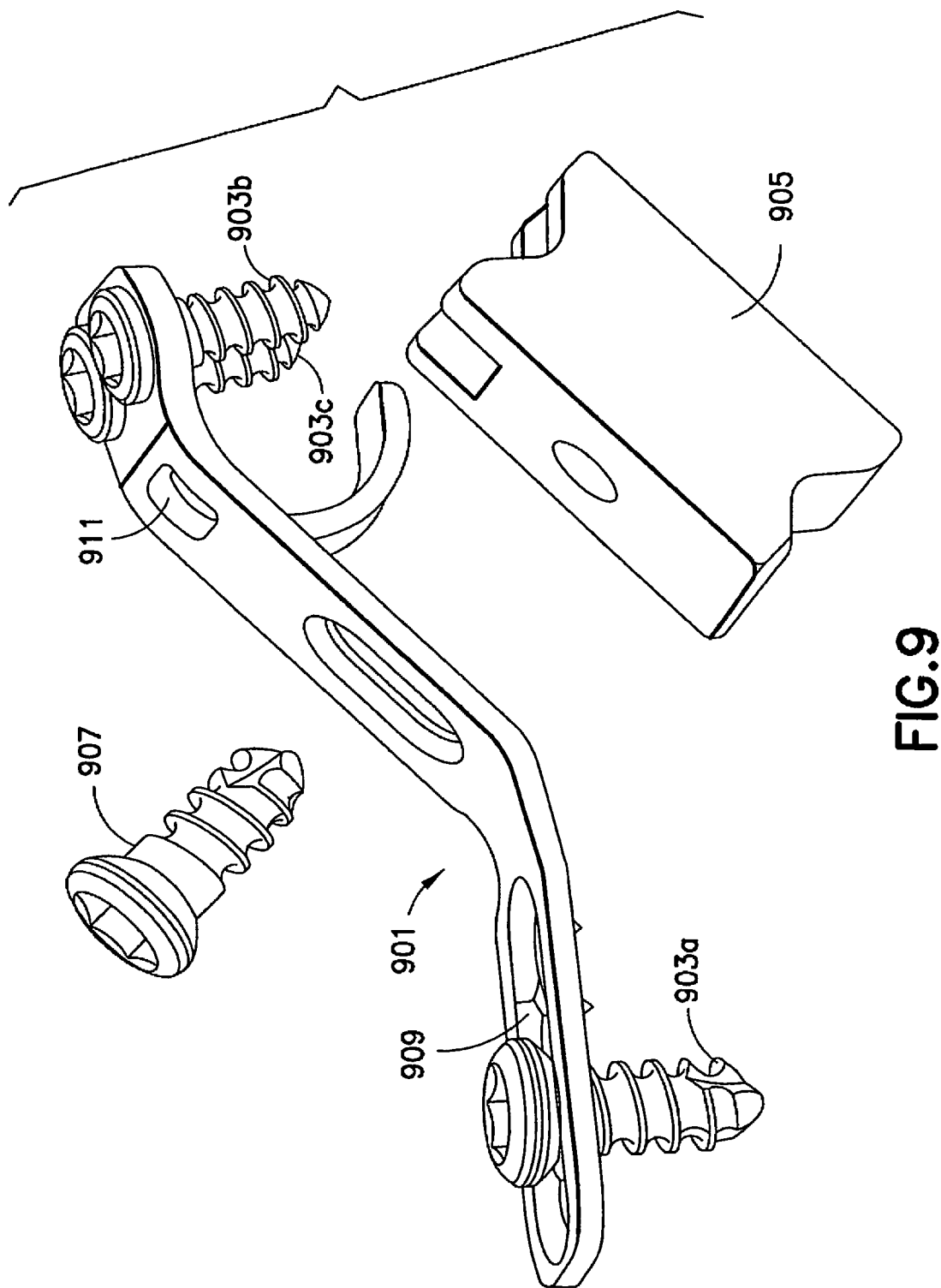
FIG. 9 shows an exploded perspective view of a bone plate apparatus according to another embodiment of the present invention.

Referring now to FIG. 9, another embodiment of a bone plate apparatus according to the present invention is shown. As seen in this Fig., Bone Plate 901 may be attached to bone using Bone Screws 903a, 903b and 903c. In one example (which example is intended to be illustrative and not restrictive), Bone Plate 901 may have a length between 20 mm and 30 mm (e.g., Bone Plate 901 may be provided in a number of distinct lengths). In another example (which example is intended to be illustrative and not restrictive), each of Bone Screws 903a, 903b and 903c may be a self-tapping bone screw. In another example (which example is intended to be illustrative and not restrictive), each of Bone Screws 903a, 903b and 903c may have a diameter selected from the group including (but not limited to) 1.5 mm, 2.0 mm and 2.7 mm. In another example (which example is intended to be illustrative and not restrictive), each of Bone Screws 903a, 903b and 903c may have a length from 4 mm to 8 mm, in 0.1 mm increments.

Further, Bone Contacting Element 905 may be held in place by Fastener 907 (e.g., a screw). This Bone Contacting Element 905 may be provided for spacing a first section of a divided lamina apart from a second section of the divided lamina following a laminoplasty procedure and/or for providing fixation of Bone Plate 901 to a first section of a divided lamina and/or a second section of the divided lamina following a laminoplasty procedure (such fixation may be provided, for example, via the mechanism of bone ingrowth).

In one example (which example is intended to be illustrative and not restrictive), Bone Contacting Element 905 may comprise bone (e.g., allograph bone).

In another example (which example is intended to be illustrative and not restrictive), Fastener 907 may be a bone screw.

Further still, Slot 909 (which may have distinct holding positions or detents (as shown in this Fig.), and/or which may not have such detents in order to allow essentially free positioning anywhere within the slot) may be provided to aid in adjustment to an individual patient's anatomy.

Further still, Hole 911 may be provided for engagement with an insertion tool (discussed in more detail below).

Further still, one or more protrusions (or "teeth") may be provided to aid in maintaining position during and/or after implantation (a number of such teeth are shown but not separately numbered in this Fig.).

Further still, the bottom profile may be streamlined as shown in this Fig. (e.g., in order to reduce the penetration inside the spine).

Figure 10C:
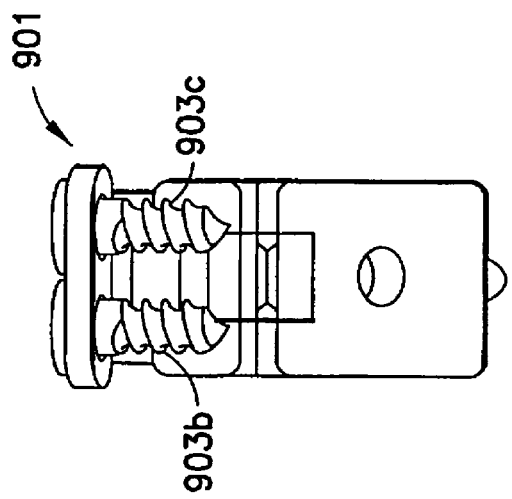
FIGS. 10A, 10B and 10C show, respectively, a plan view, a side elevational view and a front view of the bone plate apparatus of FIG. 9.
Figure 10A:
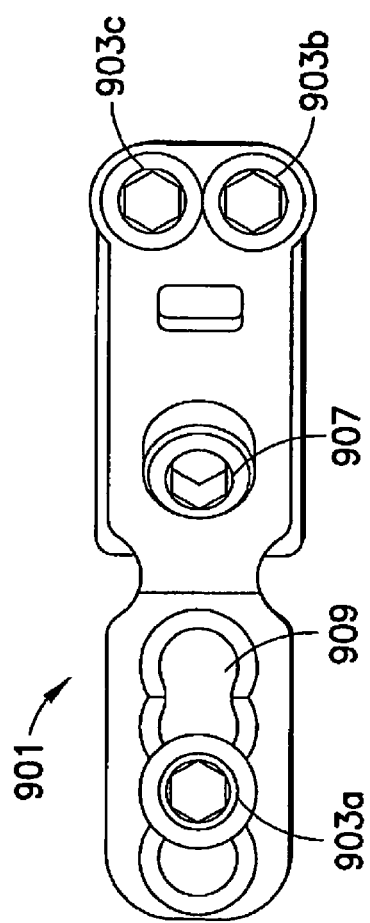
Figure 10B:
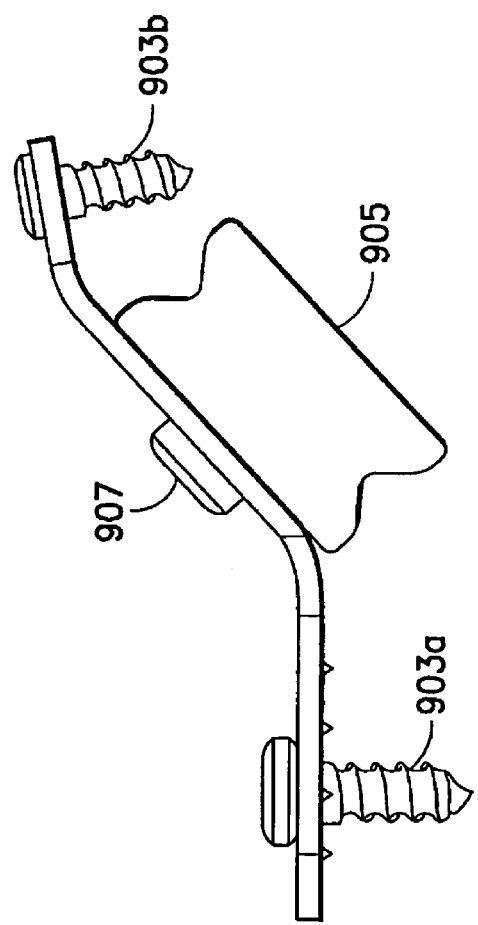
Figure 11:
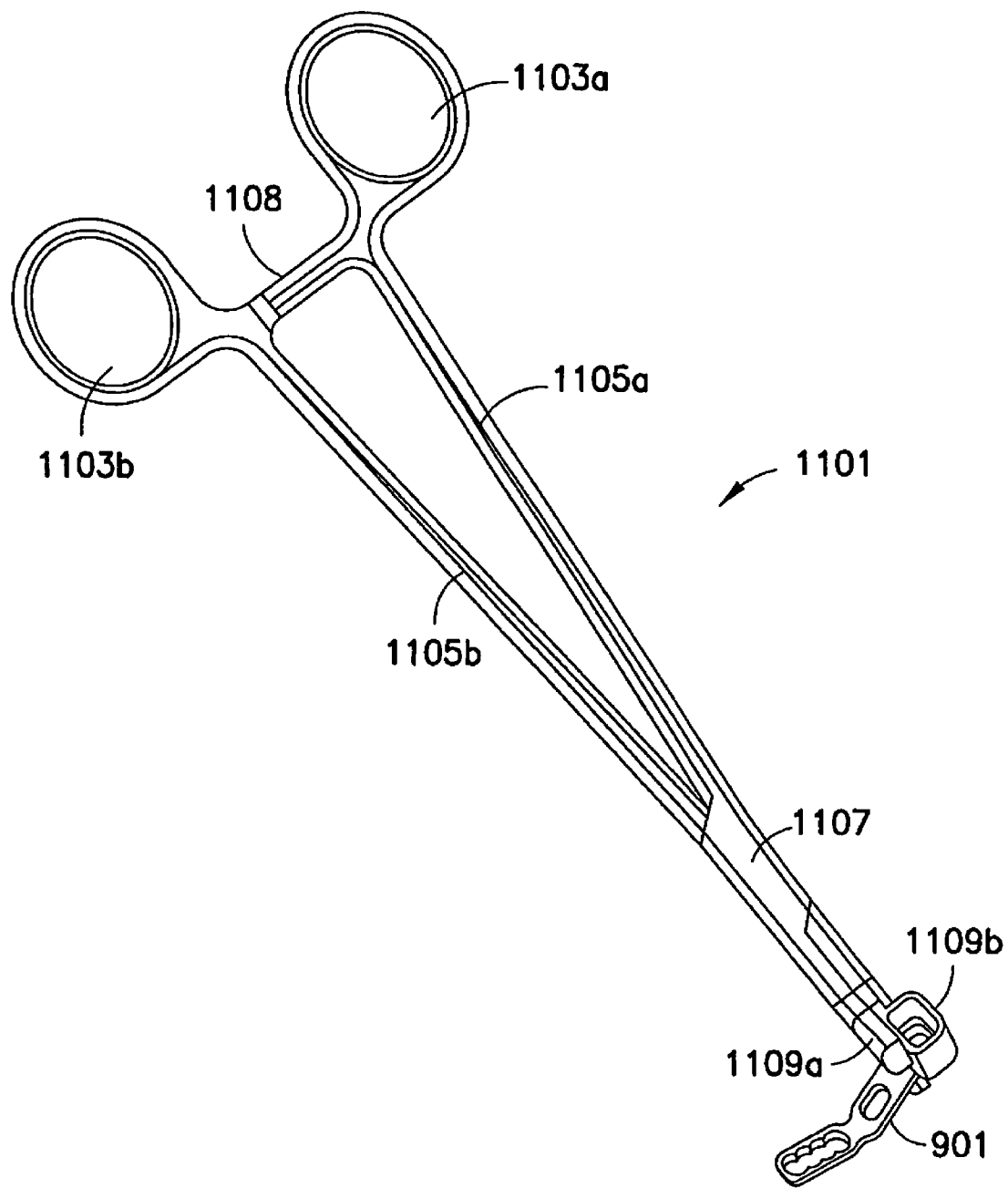
FIG. 11 shows a perspective view of a bone plate apparatus according to an embodiment of the present invention and an insertion tool associated therewith according to an embodiment of the present invention.

Referring now to FIGS. 10A, 10B and 10C, a plan view, a side elevational view and a front view of the bone plate apparatus of FIG. 9 are shown.

Referring now to FIGS. 11-14, it is seen that Insertion Tool 1101 (which may be, for example, a scissor-like device) may be used to aid insertion of Bone Plate 901 into a patient (e.g., to make placement quick and easy). Further, it is seen that Insertion Tool 1101 may include Operator Grip Elements 1103a and 1103b (e.g., finger holes), First and Second Elongated Members 1105a and 1105b, Pivot 1107 and First and Second Bone Plate Coupling Elements 1109a and 1109b. In addition, it is seen that Implantation Tool 1101 may include a releasable Ratchet Lock Mechanism 1108. Moreover, it is seen that Second Bone Plate Coupling Element 1109b may include a hole therethrough to permit one or more fasteners to be driven into the lamina through Second Bone Plate Coupling Element 1109b by any desired fastener driving device (of note, for the sake of clarity, Bone Plate 901 is shown in these FIGS. 11-14 without the associated Fasteners 903a, 903b, 903c, 907, Bone Contacting Element 905 or fastener driver device).

Figure 12:
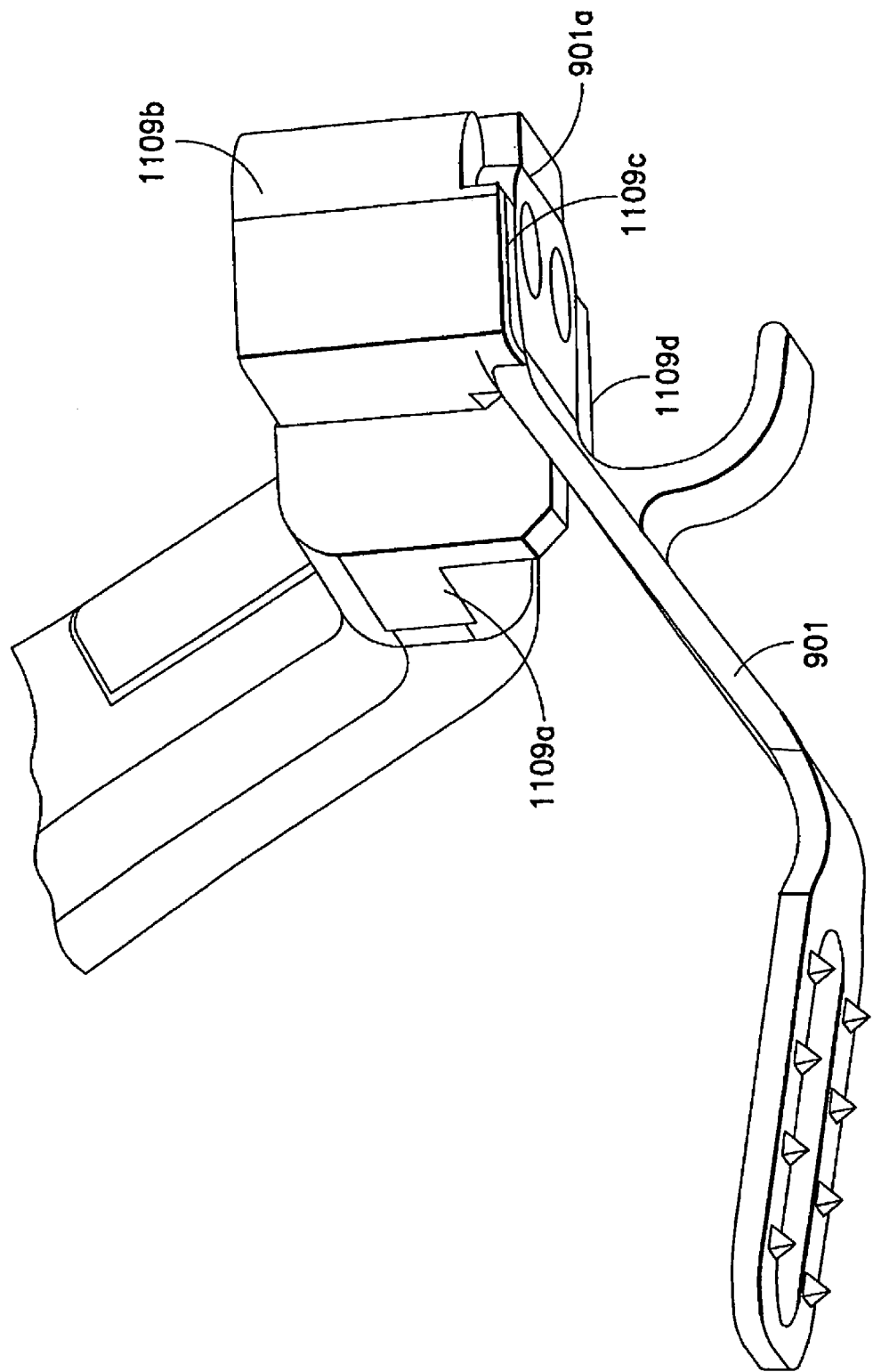
FIG. 12 shows a perspective view of the area of engagement between the bone plate apparatus and insertion tool shown in FIG. 11.
Figure 14:
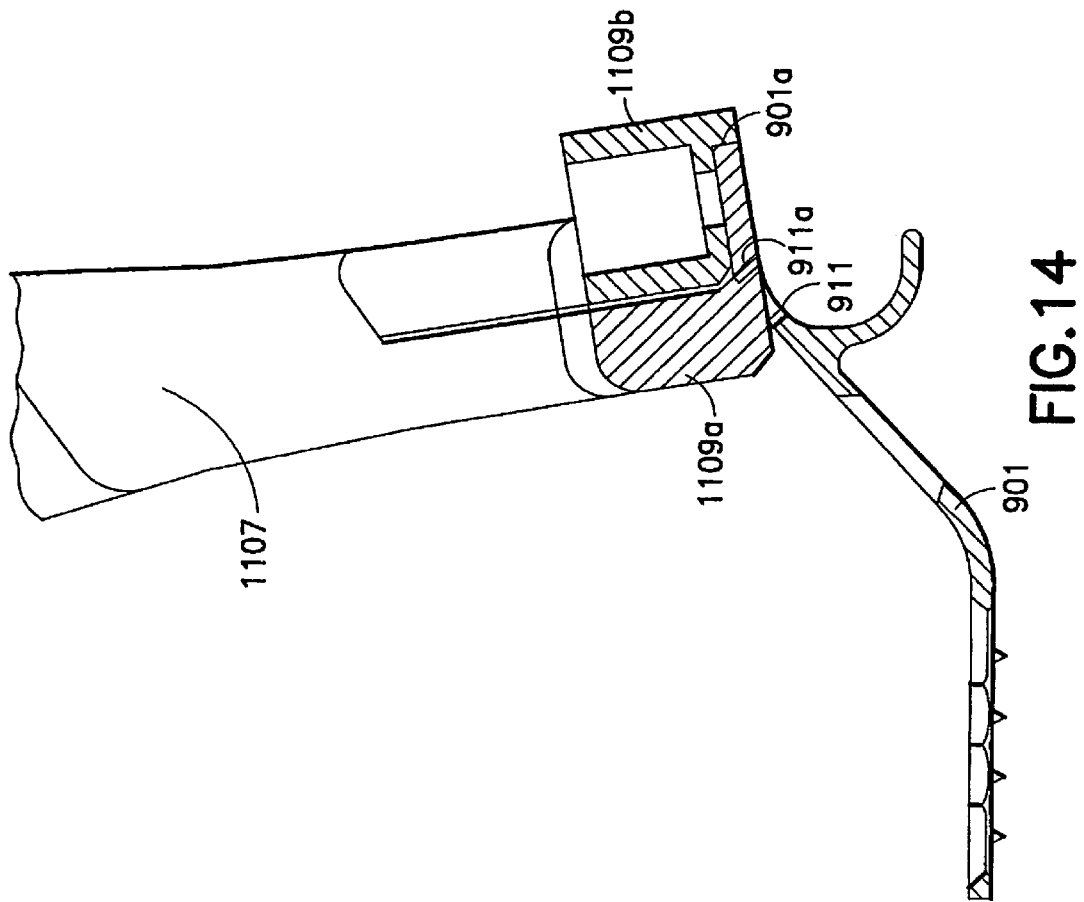
FIG. 14 shows a detailed cross-sectional view taken along the line E-E of FIG. 13.
Figure 13:
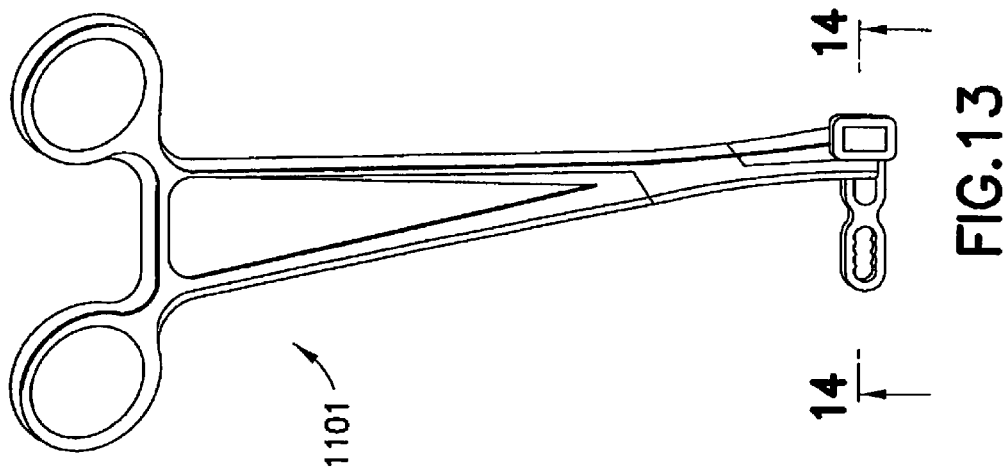
FIG. 13 shows another view of the bone plate apparatus and insertion tool shown in FIG. 11.

Referring now more particularly to FIGS. 12-14, it is seen that the coupling between Insertion Tool 1101 and Bone Plate 901 may be provided, for example, at least in part through a clamping action. That is, the coupling may result at least in part from: (a) a portion of First Bone Plate Coupling Element 1109a entering Hole 911, mating with Inner Wall 911a, and applying force towards Second Bone Plate Coupling Element 1109b; and (b) a portion of Second Bone Plate Coupling Element 1109b mating with End Face 901a and applying force towards First Bone Plate Coupling Element 1109a.

In one example (which example is intended to be illustrative and not restrictive), the coupling between Bone Plate 901 and Insertion Tool 1101 may be of a dovetail configuration, wherein Inner Wall 911a and End Face 901a slope inward and the corresponding contact areas of First Bone Plate Coupling Element 1109a and Second Bone Plate Coupling Element 1109b have a matching angle.

In another example (which example is intended to be illustrative and not restrictive), the coupling may result not so much from a clamping action between First Bone Plate Coupling Element 1109a and Second Bone Plate Coupling Element 1109b but rather due to the geometric configuration of the interface between Implantation Tool 1101 and Bone Plate 901 (e.g., due to a dovetail interface configuration which acts to affix Bone Plate 901 Implantation Tool 1101).

In another example (which example is intended to be illustrative and not restrictive), Second Bone Plate Coupling Element 1109b may include Extensions 1109c and 1109d for fixing Bone Plate 901 therein (e.g., for prohibiting Bone Plate 901 from moving laterally when engaged at Inner Wall 911a and End Face 901a (see FIG. 12).

While a number of embodiments of the present invention have been described, it is understood that these embodiments are illustrative only, and not restrictive, and that many modifications may become apparent to those of ordinary skill in the art. For example, while the present invention has been described principally with respect to three bone screws driven into the lamina, any desired number may, of course, be utilized. Further, the teeth, grooves and/or ridges may be placed at any desired position(s) on the bone plate apparatus. Further still, one or more slots may be utilized for one or more bone screws. Further still, any desired number of detents may be utilized. Further still, the angles between the portions of the bone plate may be any desired angles. Further still, any desired mechanism(s) for locking one or more bone screws relative to the bone plate may be utilized (instead of or in addition to the locking plate described above). Further still, the bone plate apparatus may, of course, have any desired dimensions (e.g., for any desired patient—man, woman or child). Further still, the bone plate apparatus of the present invention may be provided in a "line" or "family" of devices (e.g., small, medium and large; adult, child; male, female). Further still, the bone plate apparatus of the present invention may be provided in standard sizes. Further still, one or more components may be constructed of Ti, cobalt chromium, surgical steel and/or any combination thereof. Further still, a "hole" may be of any desired shape (e.g., circular, square, oval, rectangular, etc.) and may extend partially or fully through the thickness of a structure. Further still, while the hole(s) to permit the driving of the fastener(s) are shown in the Figs. in the second bone plate coupling element of the implantation tool, the device could, of course, be configured such that the hole(s) are instead (or additionally) disposed in the first bone plate coupling element of the implantation tool. Likewise, while the extension(s) are shown in the Figs. on the second bone plate coupling element of the implantation tool, the device could, of course, be configured such that the extensions(s) are instead (or additionally) disposed on the first bone plate coupling element of the implantation tool. Further still, any steps relating to manufacture and/or use may be performed in any desired order.

What is claimed is:

1. An apparatus placed by an implantation tool for spacing a first section of a divided lamina apart from a second section of the divided lamina in connection with a laminoplasty procedure, comprising:
   a first portion for attachment to the first section of the divided lamina, wherein the first portion includes at least one hole therethrough for receiving a first fastener driven into the first section of the divided lamina;
   a second portion for attachment to the second section of the divided lamina, wherein the second portion includes at least one hole therethrough for receiving a second fastener driven into the second section of the divided lamina;
   an intermediate portion connecting the first and second portions, wherein the intermediate portion connects the first and second portions such that the first and second portions are spaced apart from one another along a first axis and the first and second portions are offset from one another along a second axis which is generally perpendicular to the first axis;
   an extension connected to the intermediate portion for engaging the first section of the divided lamina;
   a receiving element for placement between the first and second section of the divided lamina, wherein the receiving element possesses a channel for receiving the extension; and
   wherein the extension and the first portion extend away from the intermediate portion and substantially toward the same direction.

2. The apparatus of claim 1, wherein an aperture defined in the intermediate portion comprises an inner wall angled inward from a top part of the inner wall to a bottom part of the inner wall to contact a first part of the implantation tool; and wherein an end face of the first portion is angled inward from a top side of the first portion to a bottom side of the first portion to contact a second part of the implantation tool.

3. The apparatus of claim 1, wherein an aperture defined in the intermediate portion is operable to be engaged by an extension member protruding from a first part of the implantation tool.

4. The apparatus of claim 1, wherein an aperture defined in the intermediate portion extends through the apparatus.

5. The apparatus of claim 1, wherein at least one of the first fastener and the second fastener is a bone screw.

6. The apparatus of claim 5, wherein at least one of the first fastener and the second fastener is a self-tapping bone screw.

7. The apparatus of claim 1, wherein the first portion includes a plurality of generally circular holes therethrough for receiving a respective plurality of fasteners driven into the first section of the divided lamina.

8. The apparatus of claim 1, wherein the second portion includes a plurality of generally circular holes therethrough for receiving a respective plurality of fasteners driven into the second section of the divided lamina.

9. The apparatus of claim 8, wherein the plurality of holes through the second portion are arranged in a generally linear pattern.

10. The apparatus of claim 1, wherein the hole of the second portion is in the form of a slot.

11. The apparatus of claim 10, wherein the slot includes at least one detent.

12. The apparatus of claim 1, wherein the receiving element is a bone growth receiving element.

13. The apparatus of claim 1, wherein the receiving element is natural bone.

14. The apparatus of claim 1, wherein the extension extends from the intermediate portion from a position between the first portion and the second portion for forming a space for receiving at least part of the first section of the divided lamina.

15. The apparatus of claim 14, wherein the extension is configured to at least partially support the first section of the divided lamina when the first fastener is driven into the first section of the divided lamina.

16. The apparatus of claim 1, wherein the apparatus comprises a material selected from the group including: (a) titanium; and (b) titanium alloy.

17. The apparatus of claim 1, wherein at least one of a surface of the first portion adjacent the first section of the divided lamina and a surface of the second portion adjacent the second section of the divided lamina is textured.

18. The apparatus of claim 17, wherein the texture aids in maintaining position of the apparatus relative to at least one of the first section of the divided lamina and the second section of the divided lamina.

19. The apparatus of claim 18, wherein the texture is selected from the group including: (a) teeth; (b) grooves; and (c) ridges.

20. The apparatus of claim 1, wherein the first and second portions are disposed generally parallel to one another.

21. The apparatus of claim 1, wherein the first and second portions are disposed at an angle relative to one another.

22. A system for spacing a first section of a divided lamina apart from a second section of the divided lamina in connection with a laminoplasty procedure, comprising:
   (i) a spacer including:
      (a) a first portion for attachment to the first section of the divided lamina, wherein the first portion includes at least one hole therethrough for receiving a first fastener driven into the first section of the divided lamina;
      (b) a second portion for attachment to the second section of the divided lamina, wherein the second portion includes at least one hole therethrough for receiving a second fastener driven into the second section of the divided lamina;
      (c) an intermediate portion connecting the first and second portions, wherein the intermediate portion connects the first and second portions such that the first and second portions are spaced apart from one another along a first axis and the first and second portions are offset from one another along a second axis which is generally perpendicular to the first axis;

(d) an extension connected to the intermediate portion and extending in a direction towards the first portion for engaging the first section of the divided lamina;
(e) a receiving element for placement between the first and second section of the divided lamina, wherein the receiving element possesses a channel for receiving the extension;
(f) an implantation tool receiving hole;
(g) an end face of the first portion; and
(ii) an implantation tool having a scissors mechanism and being formed by a first elongated element and a second elongated element secured at a pivot, wherein the implantation tool includes:
(a) a first operator grip component at a first end of the first elongated element;
(b) a second operator grip component a first end of the second elongated element;
(c) a first implant coupling component at a second end of the first elongated element;
(d) a second implant coupling component at a second end of the second elongated element;
(e) wherein the first implant coupling component is configured to engage the implantation tool receiving hole in the spacer; and
(f) wherein the second implant coupling component is configured to engage the end face of the first portion of the spacer.

23. The system of claim 22, wherein at least one of: an inner wall of a tool receiving hole angled inward from a top part of the inner wall to a bottom part of the inner wall to contact the first implant coupling component of the implantation tool; and wherein an end face of the first portion is angled inward from a top side of the first portion to a bottom side of the first portion to contact the second implant coupling component of the implantation tool.

24. The system of claim 22, wherein the spacer is removable coupled to the implantation tool by the clamping action of the first implant coupling component of the implantation tool disposed in an implantation tool receiving hole and the second implant coupling component of the implantation tool pressing against an end face of the first portion.

25. The system of claim 22, wherein the first portion of the spacer comprises two side portions extending between the intermediate portion and the end face of the first portion, wherein the implantation tool includes a first downward extension protruding from at least one of the first implant coupling component of the implantation tool and the second implant coupling component of the implantation tool, wherein the implantation tool includes a second downward extension protruding from at least one of the first implant coupling component of the implantation tool and the second implant coupling component of the implantation tool, and wherein the first and second downward extensions are configured to abut the side portions of the spacer when the implantation tool receiving hole and end face of the spacer are engaged by the implantation tool.

26. The system of claim 22, wherein at least one of the first implant coupling component of the implantation tool and the second implant coupling component of the implantation tool is configured to permit the fastener to be driven into the first section of the divided lamina while the implantation tool is coupled to the spacer.

27. The system of claim 26, wherein at least one of the first implant coupling component of the implantation tool and the second implant coupling component of the implantation tool has at least one hole therethrough to permit the fastener to be driven into the first section of the divided lamina while the implantation tool is coupled to the spacer.

28. The system of claim 27, wherein the first implant coupling component of the implantation tool has at least one hole therethrough to permit the fastener to be driven into the first section of the divided lamina while the implantation tool is coupled to the spacer.

29. The system of claim 27, wherein the second implant coupling component of the implantation tool has at least one hole therethrough to permit the fastener to be driven into the first section of the divided lamina while the implantation tool is coupled to the spacer.

30. A method for spacing a first section of a divided lamina apart from a second section of the divided lamina in connection with a laminoplasty procedure, comprising:
(i) providing a spacer including:
(a) a first portion for attachment to the first section of the divided lamina, wherein the first portion includes at least one hole therethrough for receiving a first fastener driven into the first section of the divided lamina;
(b) a second portion for attachment to the second section of the divided lamina, wherein the second portion includes at least one hole therethrough for receiving a second fastener driven into the second section of the divided lamina;
(c) an intermediate portion connecting the first and second portions, wherein the intermediate portion connects the first and second portions such that the first and second portions are spaced apart from one another along a first axis and the first and second portions are offset from one another along a second axis which is generally perpendicular to the first axis;
(d) an extension connected to the intermediate portion that extends in a direction towards the first portion for engaging the first section of the divided lamina;
(e) a receiving element for placement between the first and second section of the divided lamina, wherein the receiving element possesses a channel for receiving the extension;
(f) an implantation tool receiving hole;
(g) an end face of the first portion; and
(ii) providing an implantation tool having a scissors mechanism and being formed by a first elongated element and a second elongated element secured at a pivot, wherein the implantation tool includes;
(a) a first operator grip component at a first end of the first elongated element;
(b) a second operator grip component at a first end of the second elongated element;
(c) a first implant coupling component at a second end of the first elongated element; and
(d) a second implant coupling component at a second end of the second elongated element;
(e) wherein the first implant coupling component is configured to engage the implantation tool receiving hole in the spacer; and
(f) wherein the second implant coupling component is configured to engage the end face of the first portion of the spacer.

31. The method of claim 30, wherein the steps are carried out in the order recited.

32. An apparatus placed by an implantation tool for spacing a first section of a divided lamina apart from a second section of the divided lamina in connection with a laminoplasty procedure, comprising:

a first portion for attachment to the first section of the divided lamina, wherein the first portion includes at least one hole therethrough for receiving fasteners driven into the first section of the divided lamina;

a second portion for attachment to the second section of the divided lamina, wherein the second portion includes at least one hole therethrough for receiving a second fastener driven into the second section of the divided lamina;

an intermediate portion connecting the first and second portions, wherein the intermediate portion connects the first and second portions such that the first and second portions are spaced apart from one another along a first axis and the first and second portions are offset from one another along a second axis which is generally perpendicular to the first axis;

an extension connected to the intermediate portion for engaging the first section of the divided lamina, the extension and the first portion extending away from the intermediate portion and substantially toward the same longitudinal direction;

a receiving element for placement between the first and second section of the divided lamina, wherein the receiving element possesses a channel for receiving the extension.

33. The apparatus of claim 32, wherein the receiving element is a bone growth receiving element.

34. The apparatus of claim 32, wherein the receiving element is natural bone.

* * * * *